(12) United States Patent
Takahashi et al.

(10) Patent No.: US 7,443,480 B2
(45) Date of Patent: Oct. 28, 2008

(54) SPACER FOR LIQUID CRYSTAL DISPLAY AND PROCESS FOR PRODUCING THE SAME

(75) Inventors: Toru Takahashi, Koka-gun (JP); Motokuni Ichitani, Mishima-gun (JP); Hiroshi Yoshitani, Mishima-gun (JP)

(73) Assignee: Sekisui Chemical Co., Ltd., Osaka (JP)

( * ) Notice: Subject to any disclaimer, the term of this patent is extended or adjusted under 35 U.S.C. 154(b) by 681 days.

(21) Appl. No.: 10/522,167

(22) PCT Filed: Dec. 4, 2003

(86) PCT No.: PCT/JP03/15507

§ 371 (c)(1), (2), (4) Date: Mar. 14, 2005

(87) PCT Pub. No.: WO2004/051352

PCT Pub. Date: Jun. 17, 2004

(65) Prior Publication Data

US 2006/0087611 A1    Apr. 27, 2006

(30) Foreign Application Priority Data

Dec. 5, 2002 (JP) .............................. 2002-353989
Jun. 30, 2003 (JP) .............................. 2003-188388
Sep. 30, 2003 (JP) .............................. 2003-342206
Nov. 18, 2003 (JP) .............................. 2003-388444

(51) Int. Cl.
G02F 1/1339 (2006.01)
(52) U.S. Cl. .................... 349/155; 349/187
(58) Field of Classification Search ................ 349/155, 349/156, 157, 187
See application file for complete search history.

(56) References Cited

U.S. PATENT DOCUMENTS 5,389,288 A   2/1995   Rindo et al.
6,441,880 B1 * 8/2002 Utsumi et al. ............... 349/155

FOREIGN PATENT DOCUMENTS

| EP | 0 773 466 A1 | 5/1997 |
|---|---|---|
| JP | 5-25300 | 2/1993 |
| JP | 6-11719 | 1/1994 |

(Continued)

*Primary Examiner*—Dung T. Nguyen
*Assistant Examiner*—Tai Duong
(74) *Attorney, Agent, or Firm*—Sughrue Mion, PLLC

(57) ABSTRACT

It is an object of the present invention to provide a spacer for a liquid crystal display and a method of producing a spacer for a liquid crystal display, which improve light leakage around a spacer for a liquid crystal display in cutting off light of a liquid crystal display and in vibrating a liquid crystal display and in addition have a good dry spraying property.

The present invention relates to a spacer for a liquid crystal display, which comprises a base particle and a polymer coating the surface of said base particle, a contact angle A1 of water on the spacer, measured at 25° C. when said spacer is annealed at a temperature of an annealing temperature T1 or higher in fabricating a liquid crystal display for 1 hour or more and then cooled, and a contact angle B of water on the spacer, measured at 25° C. without annealing the spacer, satisfying the relationship of the following equation (1):

$$A1 - B \geq 1°. \quad (1)$$

19 Claims, 1 Drawing Sheet

FOREIGN PATENT DOCUMENTS

| | | |
|---|---|---|
| JP | 6-130401 A | 5/1994 |
| JP | 08-190098 A | 7/1996 |
| JP | 9-33930 A | 2/1997 |
| JP | 9-222608 | 8/1997 |
| JP | 10-226512 A | 8/1998 |
| JP | 10-324706 A | 12/1998 |
| JP | 2000-29037 A | 1/2000 |
| JP | 2001-133788 | 5/2001 |

* cited by examiner

Fig. 1

SPACER FOR LIQUID CRYSTAL DISPLAY AND PROCESS FOR PRODUCING THE SAME

TECHNICAL FIELD

The present invention relates to a spacer for a liquid crystal display and a method of producing a spacer for a liquid crystal display, which improve light leakage around a spacer for a liquid crystal display in cutting off light of a liquid crystal display and in vibrating a liquid crystal display and in addition have a good dry spraying property.

BACKGROUND ART

Generally, a liquid crystal display has a constitution in which two transparent substrates, respectively, on which a transparent electrode, an alignment layer, a color filter and a black matrix are located inside and a polarizer is located outside, are located on opposed sides through a sealing material installed at the peripheral of the transparent substrates, and liquid crystal is sealed in a gap formed. In such a liquid crystal display, spacers for a liquid crystal display are used for the purpose of regulating a spacing of two transparent substrates and maintaining a proper thickness (cell gap) of a liquid crystal layer.

As the spacer for a liquid crystal display, a particle comprising an organic material or an inorganic material is used. But, in a liquid crystal display fabricated by using such the spacer for a liquid crystal display, there has been a problem that light leakage might occur around the spacer for a liquid crystal display and the contrast of image might be deteriorated in an initial condition immediately following the production of the liquid crystal display or in applying high voltage.

Such the light leakage is considered to result from the occurrence of abnormal alignment of a liquid crystal around a spacer for a liquid crystal display. Particularly in recent years, it often becomes to perform a vibration test in which a panel of a liquid crystal display is struck or is give an impact because demands on image quality of a liquid crystal display have became stringent. In the vibration test, since a molecule of liquid crystal moves heavily, the light leakage occurs only by the slight occurrence of abnormal alignment on the surface of a spacer, and therefore this becomes a large problem.

For this situation, there is disclosed a spacer for a liquid crystal display, which is surface-treated with compounds containing a straight-chain alkyl group, in Japanese Kokai Publication Hei-9-222608. By surface-treating the spacer with such a compound containing a straight-chain alkyl group, the resulting spacer for a liquid crystal display exhibits high hydrophobicity, and therefore the abnormal alignment of a liquid crystal around a spacer for a liquid crystal display can be inhibited. But, since such a spacer for a liquid crystal display having high hydrophobicity becomes charged readily to flocculate, there is a problem that spacers can not be sprayed well by a dry spray method.

SUMMARY OF THE INVENTION

It is an object of the present invention to provide a spacer for a liquid crystal display and a method of producing a spacer for a liquid crystal display, which improve light leakage around a spacer for a liquid crystal display in cutting off light of a liquid crystal display and in vibrating a liquid crystal display and in addition have a good dry spraying property.

The present invention pertains to a spacer for a liquid crystal display, which comprises a base particle and a polymer coating the surface of the above-mentioned base particle, a contact angle $A1$ of water on the spacer, measured at 25° C. when the spacer is annealed at a temperature of an annealing temperature $T1$ or higher in fabricating a liquid crystal display for 1 hour or more and then cooled, and a contact angle $B$ of water on the spacer, measured at 25° C. without annealing the spacer, satisfying the relationship of the following equation (1):

$$A1-B \geq 1° \tag{1}$$

In the spacer for a liquid crystal display of the present invention, wherein, preferably, a contact angle $A1$ of water on the spacer, measured at 25° C. when the spacer is annealed at a temperature of an annealing temperature $T1$ or higher in fabricating a liquid crystal display for 1 hour or more and then cooled, and a contact angle $B$ of water on the spacer, measured at room temperature without annealing the spacer, satisfy the relationship of the following equation (2):

$$A1-B \geq 8° \tag{2}$$

The present invention pertains to a spacer for a liquid crystal display, which comprises a base particle and a polymer coating the surface of the above-mentioned base particle, a contact angle $A2$ of water on the spacer, measured at 25° C. when the spacer is annealed at a temperature of a glass transition temperature $T2$ or higher of the above polymer and then cooled, and a contact angle $B$ of water on the spacer, measured at 25° C. without annealing the spacer, satisfying the relationship of the following equation (3):

$$A2-B \geq 1° \tag{3}$$

In the spacer for a liquid crystal display of the present invention, wherein, preferably, a contact angle $A2$ of water on the spacer, measured at 25° C. when the spacer is annealed at a temperature of a glass transition temperature $T2$ or higher of the polymer and then cooled, and a contact angle $B$ of water on the spacer, measured at 25° C. without annealing the spacer, satisfy the relationship of the following equation (4):

$$A2-B \geq 8° \tag{4}$$

Preferably, the above-mentioned polymer contains a component containing an alkyl group having 10 or more carbon atoms in an amount 10% by weight or more and a component containing an alkyl group having 4 or less carbon atoms in an amount 50% by weight or more.

A method of producing a spacer for a liquid crystal display of the present invention, comprising the steps of coating the surface of a base particle with a polymer, and immersing the above-mentioned base particle, the surface of which is coated with the above-mentioned polymer, in a liquid medium having a SP value of 10 or higher and then drying the base particle, also constitutes the present invention. The above-mentioned liquid medium having a SP value of 10 or higher preferably has a SP value of 12 to 15 and preferably contains methanol in an amount 50% by weight or more.

A liquid crystal display, which is obtainable by using the spacer for a liquid crystal display of the present invention, also constitutes the present invention.

A method of measuring the contact angle of water on spacers for a liquid crystal display, in which a water droplet is formed on the surface obtainable by arraying an abundance of spacers for a liquid crystal display without being observed projections and depressions of 50 μm or larger on the surface and the contact angle of water on the above surface is measured, also constitutes the present invention.

BRIEF DESCRIPTION OF THE DRAWINGS

In FIG. 1, a reference numeral 1 denotes a spacer for a liquid crystal display, and reference numerals 2 and 3 denote a pseudo plane and a water droplet, respectively.

DETAILED DESCRIPTION OF THE INVENTION

Hereinafter, the present invention will be described in detail.

A spacer for a liquid crystal display of the present invention comprises a base particle and a polymer which coats the surface of the base particle and a contact angle A1 of water on the spacer, measured at 25° C. when the spacer is annealed at a temperature of an annealing temperature T1 or higher in fabricating a liquid crystal display for 1 hour or more and then cooled, and a contact angle B of water on the spacer, measured at 25° C. without annealing the spacer, satisfy the relationship of the following equation (1).

$$A1-B \geqq 1° \quad (1)$$

As a result of an intense study, the present inventors have found that when A1 and B satisfy the relationship of the above equation (1), a condition that the spacer for a liquid crystal display hardly generates abnormal alignment of a liquid crystal around a spacer for a liquid crystal display and degradation of images due to a light leakage is compatible with a condition that the spacers can be sprayed well by a dry spray method. When a value of A1–B is less than 1°, the contact angle of water on the spacer after annealing is small and therefore the abnormal alignment of a liquid crystal is apt to occur, or the contact angle of water on the not-yet-annealed spacer is large and therefore spacers cannot be sprayed by a dry spray method since the spacers are apt to become charged to flocculate. Particularly, when A1 and B satisfy the relationship of the following equation (2), the spacer for a liquid crystal display of the present invention can be suitably used for not only a liquid crystal display of a TN mode but also a liquid crystal display of a VA mode, which requires higher performances.

$$A1-B \geqq 8° \quad (2)$$

In addition, in the present specification, the term "annealing in fabricating a liquid crystal display" means an operation by which a liquid crystal is modified once from a liquid crystal condition to an isotropic condition in a step of assembling the liquid crystal display to bring the liquid crystal in an initial condition and an annealing temperature in fabricating a liquid crystal display is generally a temperature of the order of 50 to 100° C., which is higher than a glass transition temperature of a surface treated layer of the spacer.

A spacer for a liquid crystal display of the present invention comprises a base particle and a polymer which coats the surface of the base particle and a contact angle A2 of water on the spacer, measured at 25° C. when the spacer is annealed at a temperature of a glass transition temperature T2 or higher of the polymer and then cooled, and a contact angle B of water on the spacer, measured at 25° C. without annealing the spacer, satisfy the relationship of the following equation (3).

$$A2-B \geqq 1° \quad (3)$$

As a result of an intense study, the present inventors have found that when A2 and B satisfy the relationship of the above equation (3), a condition that the spacer for a liquid crystal display hardly generates abnormal alignment of a liquid crystal around a spacer for a liquid crystal display and degradation of images due to a light leakage is compatible with a condition that the spacers can be sprayed well by a dry spray method. When a value of A2–B is less than 1°, the contact angle of water on the spacer after annealing the spacers at a temperature of a glass transition temperature or higher of the above polymer is small and therefore the abnormal alignment of a liquid crystal is apt to occur, or the contact angle of water on the spacer not-yet-annealed at a temperature of a glass transition temperature or higher of the above polymer is large and therefore spacers cannot be sprayed by a dry spray method since the spacers are apt to become charged to flocculate. Particularly, when A2 and B satisfy the relationship of the following equation (4), the spacer for a liquid crystal display of the present invention can be suitably used for not only a liquid crystal display of a TN mode but also a liquid crystal display of a VA mode, which requires higher performances.

$$A2-B \geqq 8° \quad (4)$$

Further, a glass transition temperature T2 of the above polymer may be determined by actual measurement, but if the actual measurement is difficult, it may be derived by calculation based on Fox's expression represented by the following equation (5).

$$1/T = Xa/Ta + Xb/Tb + Xc/Tc + \quad (5)$$

In the formula (5), T is a glass transition temperature (absolute temperature K) of a polymer, Xa is a ratio (weight ratio) of a polymerizable monomer component a, which constitutes the polymer, and Ta is a glass transition temperature (absolute temperature K) of a polymer comprising only a component a. Further, if there are another component b, component c, etc., the same can be said of these components and all polymerizable monomers constituting the polymer are used for this calculation.

The glass transition temperature T2 of the above polymer can be assumed to be a glass transition temperature derived from the above Fox's expression but, actually, the glass transition temperature may become higher than the assumed temperature due to crosslinking during polymerization in the surface of a base particle. Therefore, since the actual glass transition temperature T2 of a polymer may be higher than a glass transition temperature derived from the above Fox's expression, it is preferred to adopt a temperature, which is furthermore higher than the glass transition temperature derived from the above Fox's expression, as a temperature of a glass transition temperature T2 or higher of the above polymer.

Figure 1:
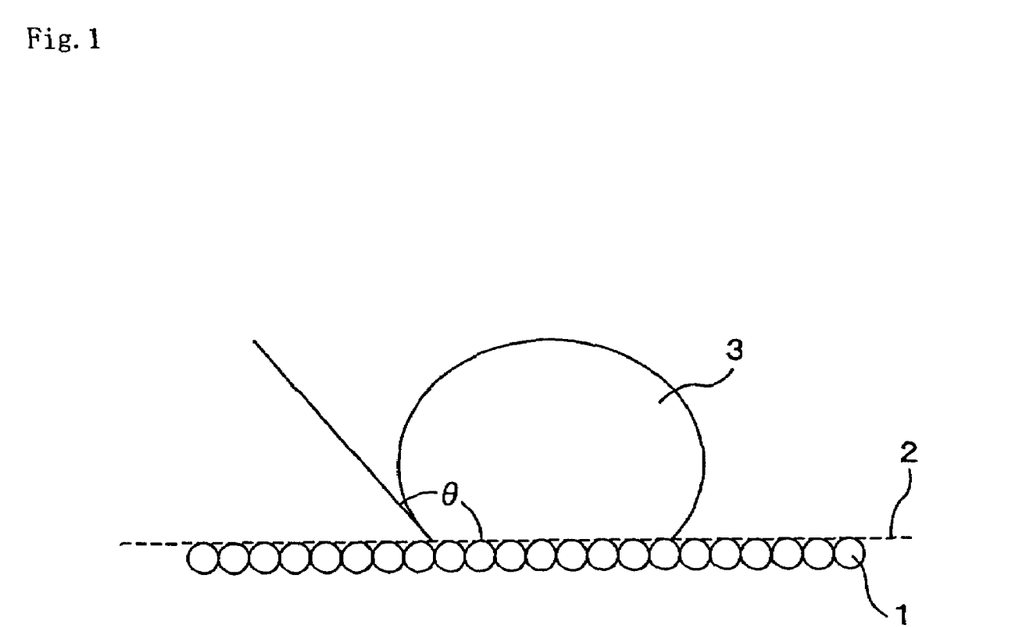
FIG. 1 is a schematic view illustrating a contact angle of water on spacers for a liquid crystal display.

Next, a measuring method of a contact angle of water on the spacers for a liquid crystal display of the present invention will be described. In this specification, the term "a contact angle of water on the spacers for a liquid crystal display" refers to a contact angle of water on a pseudo plane in considering a state, in which an abundance of spacers for a liquid crystal display are densely arrayed in one plane to the extent that it is possible to assume that a plane is substantially formed, specifically an abundance of spacers for a liquid crystal display arrayed to the extent that projections and depressions of 50 μm or larger are not observed on the surface as a plane (a pseudo plane). A schematic view illustrating the contact angle of water on the spacers for a liquid crystal display is shown in FIG. 1. In FIG. 1, when a water droplet 3 is formed on the pseudo plane 2 formed by arraying an abundance of spacers for a liquid crystal display 1 to the extent that projections and depressions of 50 μm or larger are not observed on the surface, the angle (θ), which a tangent of the droplet 3 forms with the pseudo plane 2, is assumed as a contact angle. A layer of the spacers for a liquid crystal display 1 forming the above pseudo plane may be single-layer or multiplayer, but a multiplayer is easier to make samples and to measure. In addition here, the term "the extent that projections and depressions of 50 μm or larger are not observed on the surface" means that the difference in height between ups and downs in a profile in a plane perpendicular to the above pseudo plane is 50 μm or smaller. This condition can be found through observation with a microscope. If there are projections and depressions of 50 μm or larger, the accuracy of measuring the contact angle may be poor.

The above-mentioned method of forming the pseudo plane by arraying an abundance of spacers for a liquid crystal display to the extent that projections and depressions of 50 μm or larger are not observed on the surface is not particularly limited and includes, for example, a method of forming an adhesive layer on a smoothed sample stage and arraying spacers for a liquid crystal display on the adhesive layer; and a method in which a groove with a certain depth is formed on the surface of a smoothed sample stage by etching or machining and after spraying the spacers for a liquid crystal display over the whole surface of this groove, a substance with smoothed surface such as a slide glass is pressed against the spacers and slid while being pressed against the spacers.

Water is gently dropped onto the pseudo plane, which is formed by arraying an abundance of spacers for a liquid crystal display to the extent that projections and depressions of 50 μm or larger are not observed on the surface like this, to produce a water droplet having a size of about 1.5 mm, and the contact angle of the water droplet can be measured while recognizing the water droplet with a monitor using an instrument for measuring contact angles (for example, "CONTACT ANGLE MEASURING SYSTEM G2" manufactured by KRUSS GmbH). A temperature in measuring the contact angle on the spacer for a liquid crystal display of the present invention is not particularly limited because the contact angle can be measured as long as it is a temperature at which the water droplet can be formed, but it is set at 25° C. in order to obtain desired measurements.

Such a method of measuring the contact angle of water on the spacers for a liquid crystal display, in which a water droplet is formed on the surface formed by arraying an abundance of spacers for a liquid crystal display to the extent that projections and depressions of 50 μm or larger are not observed on the surface and the contact angle of water on the above surface is measured, also constitutes the present invention.

The spacer for a liquid crystal display of the present invention comprises a base particle and a polymer which coats the surface of the above-mentioned base particle.

The above-mentioned base particle is not particularly limited and either of a particle comprising an inorganic material or a particle comprising an organic material may be used, but the particle comprising an organic material is preferred because of being able to select the material having a thermal expansion coefficient close to that of a liquid crystal and hardly generating defects such as low temperature foaming.

As the above-mentioned inorganic material constituting the base particle is not particularly limited and includes, for example, silicate glass, borosilicate glass, lead glass, soda-lime glass, alumina and alumina silicate.

As the above-mentioned organic material constituting the base particle is not particularly limited and includes, for example, polymers which are obtained by polymerizing monomers containing an ethylenically unsaturated group, e.g., epoxy resins, phenolic resins, melamine resins and unsaturated polyester resins. Among others, at least 20 weight % of a polymerizable monomer containing the above-mentioned ethylenically unsaturated group, which is the polymers obtained by polymerizing monomers containing an ethylenically unsaturated group, is preferably a polymerizable monomer containing two or more ethylenically unsaturated groups because of high mechanical strength.

The above-mentioned polymerizable monomer containing two or more ethylenically unsaturated groups is not particularly limited and includes, for example, polyfunctional (meth)acrylates such as tetramethylolmethane tetra(meth)acrylate, tetramethylolmethane tri(meth)acrylate, tetramethylolmethane di(meth)acrylate, trimethylolpropane tri(meth)acrylate, dipentaerythritol hexa(meth)acrylate, dipentaerythritol penta(meth)acrylate, glycerol tri(meth)acrylate, glycerol di(meth)acrylate, polyethylene glycol di(meth)acrylate and polypropylene glycol di(meth)acrylate; triallyl isocyanurate and triallyl trimellitate; and divinylbenzene, diallyl phthalate and diallyl acrylamide. Incidentally, in this specification, the term (meth)acrylate refers to acrylate or methacrylate.

In the case where the above base particle comprises a polymer which are obtained by polymerizing monomers containing an ethylenically unsaturated group, the above base particle may be a compound comprising only the polymerizable monomer containing two or more ethylenically unsaturated groups or may be a compound obtained by copolymerizing the polymerizable monomer containing two or more ethylenically unsaturated groups and another polymerizable monomer containing an ethylenically unsaturated group.

The above-mentioned another polymerizable monomer containing an ethylenically unsaturated group is not particularly limited and includes, for example, styrenic monomers such as styrene, α-methyl styrene and the like, and (meth)acrylates such as methyl (meth)acrylate and the like. The above polymerizable monomer containing two or more ethylenically unsaturated groups and the above another polymerizable monomer containing an ethylenically unsaturated group may be used alone or in combination of two or more species of them.

The above base particle may be colorless and transparent or may be colored by a publicly known method such as coloring by using dye as required. The above-mentioned dye is not particularly limited and includes, for example, organic pigment such as aniline black, phthalocyanine-based dyes, anthraquinone-based dyes and diazo-based dyes; inorganic pigment such as carbon black, surface modification coating materials and metal salts; and various dyes.

A method of obtaining the above base particle is not particularly limited and the above base particle can be produced by publicly known methods such as suspension polymerization, emulsion polymerization or the like.

The polymer coating the surface of the above-mentioned base particle is not particularly limited but it preferably contains a component containing an alkyl group having 10 or more carbon atoms in an amount 10% by weight or more and a component containing an alkyl group having 4 or less carbon atoms in an amount 50% by weight or more.

The above-mentioned component containing an alkyl group having 10 or more carbon atoms contributes to a vertical alignment regulation force of spacers for a liquid crystal display on a liquid crystal, and when the content of this component is less than 10% by weight, the vertical alignment regulation force is low and this causes abnormal alignment of a liquid crystal and therefore light leakage may not be prevented. The above-mentioned alkyl group having 10 or more carbon atoms is not particularly limited and includes, for example, a n-decyl group, a n-lauryl group, a n-cetyl group and a n-stearyl group. These alkyl groups having 10 or more carbon atoms may be used alone or in combination of two or more species.

On the other hand, the component containing an alkyl group having 4 or less carbon atoms contributes to a horizontal alignment regulation force of spacers for a liquid crystal display on a liquid crystal, and when the content of this component is less than 50% by weight, the horizontal alignment regulation force is low and this causes abnormal alignment of a liquid crystal and therefore light leakage may not be prevented. The above-mentioned alkyl group having 4 or less carbon atoms is not particularly limited and includes, for example, a methyl group, an ethyl group, a propyl group, a n-butyl group, an isobutyl group and a t-butyl group. These alkyl groups having 4 or less carbon atoms may be used alone or in combination of two or more species.

Thus, the above polymer will have an alignment regulation force which is about intermediate between the vertical and the horizontal alignment regulation forces by combining the component containing an alkyl group having 10 or more carbon atoms (relatively long) and the component containing an alkyl group having 4 or less carbon atoms (relatively short) and therefore a high effect of preventing the light leakage can be attained. A combination of the above alkyl group having 10 or more carbon atoms and the above alkyl group having 4 or less carbon atoms is not particularly limited and several kinds of combinations may be used in combination.

As the component containing the above-mentioned alkyl group, for example, polymerizable monomers containing an alkyl group or the like are given and specifically acrylates or methacrylates, comprising the above alkyl group, are given.

Since cell gaps of liquid crystal displays used generally are within the range of 1 to 10 μm, the spacer for a liquid crystal display of the present invention preferably has an average particle diameter of 1 to 10 μm in order to form the cell gap.

In the spacer for a liquid crystal display of the present invention, it is preferred that a CV value of the average particle diameter is 10% or lower. When it is higher than 10%, a precise cell gap may not be formed. More preferably, it is 5% or lower.

A method of producing a spacer for a liquid crystal display of the present invention is not particularly limited, but for example, a method, comprising the steps of coating the surface of a base particle with a polymer and immersing the above-mentioned base particle, the surface of Which is coated with the above-mentioned polymer, in a liquid medium having a SP value of 10 or higher and then drying the base particle, is suitable.

The method of producing a spacer for a liquid crystal display of the present invention, comprising the steps of coating the surface of a base particle with a polymer, and immersing the above-mentioned base particle, the surface of which is coated with the above-mentioned polymer, in a liquid medium having a SP value of 10 or higher and then drying the base particle, also constitutes the present invention.

The production method of a spacer for a liquid crystal display of the present invention includes a step of coating the surface of a base particle with a polymer. The above-mentioned method of coating a base particle with a polymer is not particularly limited and includes, for example, a method in which after impregnating the surface of a base particle containing a reducing group with a polymerizable monomer containing an alkyl group, radicals are generated on the surface of the above-mentioned base particle by reacting the impregnated surface with an oxidizer such as cerium salt, persulfate, etc., and a graft polymerization layer is formed on the surface of the spacer using the radical as a starting point.

The production method of a spacer for a liquid crystal display of the present invention includes a step of immersing the base particle, the surface of which is coated with the polymer, in a liquid medium having a SP value of 10 or higher and then drying the base particle. By immersing the base particle in a liquid medium having a SP value of 10 or higher, it is possible to exert characteristics on the contact angle of water described above. The reason for this is considered as follows. By immersing the spacer in the liquid medium with a SP value of 10 or higher, which has low hydrophobicity, an alkyl group of 10 or more carbon atoms, having high hydrophobicity, contained in the above polymer becomes a state of being oriented inwardly rather to the surface. Accordingly, when the spacer is dried in this state, the amount of the alkyl group of 10 or more carbon atoms, having high hydrophobicity, is less in the outermost layer of the spacer for a liquid crystal display to be obtained and therefore the contact angle of water on the spacer becomes small. On the other hand, when the spacer is heated to a temperature of a glass transition temperature or higher of the above polymer in annealing, the fluidity of the above polymer is enhanced. In this time, the alkyl group having 10 or more carbon atoms moves outward since its existence oriented outwardly is more stable than that oriented inwardly in terms of energy because of the high hydrophobicity of outside air. Accordingly, it is considered that the spacer becomes a state, in which the alkyl groups of 10 or more carbon atoms, having high hydrophobicity, gather in the surface of the spacer for a liquid crystal display through heating in annealing, and therefore the contact angle of water on the spacer becomes large.

Incidentally, the term "immersing the base particle in a liquid medium having a SP value of 10 or higher" described above refers to immersing the above base particle, the surface of which is coated with a polymer, for from several tens minutes to several hours in the above-mentioned liquid medium as distinct from the cleaning and filtering steps of the order of several minutes in production of the conventional spacers for a liquid crystal display.

When a liquid medium having a SP value of less than 10 is used, such an effect cannot be attained and in addition a surface treated layer can be impaired. The liquid medium with a SP value of 12 to 15 is preferably used. When the liquid medium with a SP value of 12 or higher is used, the above-mentioned effect is attained more surely, but in the case of a SP value of higher than 15, many liquid mediums have a high boiling point and it becomes necessary to dry the spacer by heating to a temperature of a glass transition temperature or higher of a polymer coating the surface of the base particle. Therefore, the spacer becomes a state, in which the alkyl groups of 10 or more carbon atoms, having high hydrophobicity, gather in the surface of the spacer for a liquid crystal display and the contact angle of water on the spacer becomes large, and it can become difficult to attain a good spraying property.

Further, in the present invention, a SP value of a liquid medium refers to a solubility parameter. The above-mentioned liquid medium having a SP value of 10 or higher is not particularly limited and includes, for example, dioxane (SP value=10.3), t-butanol (SP value=10.6), 2-propanol (SP value=11.4), acetonitrile (SP value=11.9), ethanol (SP value=12.7), methanol (SP value=14.5), water (SP value=23.4), etc. This liquid medium may be used alone or in combination of two or more species of them. Particularly, the above-mentioned liquid medium preferably contains methanol in an amount 50% by weight or more. By containing methanol in an amount 50% by weight or more, it becomes easy to evaporate and remove the liquid medium in a drying step after immersion in the liquid medium.

The above-mentioned method of drying is not particularly limited and evaporation of the medium may be accelerated by using an auxiliary technique such as air blowing, heating, evacuating, etc. in combination as required. However, there is used in heating a temperature of the extent that the above polymer does not melt.

Since the spacers for a liquid crystal display of the present invention has the performance described above, they can be easily sprayed by means of a dry spray method and a liquid crystal display obtained by using this method less causes the light leakage around a spacer even in cutting off light of a liquid crystal display and in vibrating a liquid crystal display.

The spacer for a liquid crystal display of the present invention can be suitably used for a liquid crystal display of a TN mode, and when it is constant, the spacer can be also suitably used for a liquid crystal display of a VA mode.

The above-mentioned liquid crystal display of a TN mode is one in which a cell is constructed in such a way that the alignment of liquid crystal molecules are different from each other by 90° on two transparent electrodes to which alignment treatment is applied in such a way that a major axis of each liquid crystal molecule is parallel to an electrode surface. When voltage is not applied, liquid crystal molecules exhibit a state of alignment, in which the major axes of molecules are continuously twisted by 90° from one electrode toward the other electrode, and light is transmitted, and when voltage is applied, a major axis of each liquid crystal molecule is oriented in the direction perpendicular to the electrode and each liquid crystal displays in response to cutoff of light. The above liquid crystal display of a VA mode is one which aligns each liquid crystal in the direction perpendicular to a panel surface in not applying voltage and drives each liquid crystal so as to incline in a horizontal direction in applying voltage by using a liquid crystal having negative dielectric anisotropy and a vertical alignment layer.

A liquid crystal display obtainable by using the spacer for a liquid crystal display of the present invention also constitutes the present invention.

A method of fabricating the liquid crystal display of the present invention is not particularly limited and the liquid crystal display can be fabricated, for example, by a method comprising the steps of spraying the spacers for a liquid crystal display of the present invention with a dry sprayer (for example, "DISPA-μA" manufactured by Nisshin Engineering Inc. etc.) and annealing the spacers by heating after spraying.

BEST MODES FOR CARRYING OUT THE INVENTION

Hereinafter, the present invention will be described in more detail by way of examples, but the present invention is not limited to these examples.

EXAMPLE 1

(1) Preparation of Base Particles 100 parts by weight of divinylbenzene (DVB) and 2 parts by weight of benzoyl peroxide (BPO) were added to 800 parts by weight of a 3% aqueous solution of polyvinyl alcohol having a saponification degree of 87.9% (PVA, "GH-20" produced by Nippon Synthetic Chemical Industry Co., Ltd.) to form a mixture and the mixture was stirred with a homogenizer to adjust the particle size thereof and then a reaction was conducted at 90° C. for 15 hours under nitrogen flow. The reactant was washed, and then classified to obtain base particles having an average particle diameter of 4 μm and a CV value of 3%.

(2) Preparation of a Spacer for a Liquid Crystal Display

Into a separable flask, 50 parts by weight of the obtained base particles, 150 parts by weight of dimethylformamide (DMF), 10 parts by weight of methyl methacrylate (MMA) containing an alkyl group having 1 carbon atom, 70 parts by weight of isobutyl methacrylate (IBM) containing an alkyl group having 4 carbon atoms and 20 parts by weight of lauryl acrylate (LA) containing an alkyl group having 12 carbon atoms were charged and adequately dispersed with a sonicater, and then the mixture was stirred uniformly. After a nitrogen gas was introduced into a reaction system to adjust a system temperature to 50° C., a solution obtainable by dissolving 2.15 g of cerium ammonium nitrate in 100 g of 1N aqueous solution of nitric acid was added to this mixture and a reaction was continued for 4 hours.

After the completion of the reaction, the reactant was washed and further immersed in methanol (SP value=14.5) and subjected to a replacement reaction by a solvent by being stirred for 12 hours in this state, and then dried to obtain a spacer for a liquid crystal display. And, a glass transition temperature of a coated polymer was 41° C. as a result of calculating according to the above equation (5).

(3) Fabrication of a Liquid Crystal Display

A liquid crystal display of a TN mode was fabricated using the obtained spacer for a liquid crystal display. As an alignment layer, SE-7210 (produced by Nissan Chemical Industries, Ltd.) was used, individual rubbing treatment of an upper and a lower substrates was applied in opposite directions, and the direction of a transmission axis of polarization of a polarizer was set at an angle of 45 degrees relative to the direction of rubbing and crossed Nicols was selected as the polarizer.

Spraying of the spacers for a liquid crystal display was conducted by means of a dry spray method using a spacer sprayer "DISPA-μA" manufactured by Nisshin Engineering Inc., and "LIXON JC-5007" produced by CHISSO CORPORATION was filled as liquid crystal and then annealed in the conditions of at 85° C. for 1 hour.

EXAMPLE 2

Spacers for a liquid crystal display and a liquid crystal display were obtained by the same procedure as in Example 1 except for continuing a reaction for 6 hours in Separation of a spacer for a liquid crystal display.

COMPARATIVE EXAMPLE 1

Spacers for a liquid crystal display and a liquid crystal display were obtained by the same procedure as in Example 1 except for continuing a reaction for 2 hours in preparation of a spacer for a liquid crystal display.

(Evaluations)

Evaluations were performed by the following methods on the spacers for a liquid crystal display and the liquid crystal displays obtained in Examples 1, 2 and Comparative Example 1. The results of evaluations are shown in Table 1.

(Measurement of Contact Angles of Water on the Spacers for a Liquid Crystal Display Before and After Annealing)

A groove of 200 μm in depth was formed on the smoothed surface of glass by etching and after filling the spacers for a liquid crystal display in this groove, a pseudo plane, in which the spacers for a liquid crystal display were arrayed, was produced by pressing the spacers with a slide glass and sliding the slide glass while pressing the spacers. As a result of observing the surface of the pseudo plane with a microscope, it could be found that the spacers for a liquid crystal display formed a plurality of layers and the spacers for a liquid crystal display of the outermost layer aligned in close contact with one another.

A water droplet was formed on this pseudo plane in such a way that its diameter was about 1.5 mm, and a contact angle of the water droplet was measured while recognizing the water droplet with a monitor using CONTACT ANGLE MEASURING SYSTEM G2 (manufactured by KRUSS GmbH). Incidentally, measurement of the contact angle was performed at room temperature of 25° C.

(B) with respect to the not-yet-treated spacers for a liquid crystal display and (A1) with respect to the annealed spacers for a liquid crystal display, which had been annealed at 85° C. for 1 hour and then cooled to 25° C., were respectively measured, and a difference between the contact angles before and after annealing (A1−B) was determined.

(Evaluation of a Spraying Property of Spacers for a Liquid Crystal Display)

Status in spraying the spacers in fabrication of a liquid crystal display was visually observed.

(Evaluation of Light Leakage of a Liquid Crystal Display)

The extent of light leakage of the liquid crystal display in cutting off light was visually observed. And in a vibration test, the extent of light leakage in striking the liquid crystal display for 1 minute with a hammer was visually observed.

and subjected to a replacement reaction by a solvent by being stirred for 12 hours in this state, and then dried to obtain a spacer for a liquid crystal display. And, a glass transition temperature of a coated polymer was 23° C. as a result of calculating according to the above equation (5).

(3) Fabrication of a Liquid Crystal Display

A liquid crystal display of a VA mode was fabricated using the obtained spacer for a liquid crystal display. As an alignment layer, there was used a solution obtainable by adding 1% of octadecyltrimethylammonium chloride to 3% aqueous solution of polyvinyl alcohol, and the direction a transmission axis of polarization of a polarizer was set at an angle of 45 degrees relative to the direction of rubbing and crossed Nicols was selected as the polarizer.

Spraying of the spacers for a liquid crystal display was conducted by means of a dry spray method using a spacer sprayer "DISPA-μA" manufactured by Nisshin Engineering Inc., and "MLC-6610" produced by Merck & Co., Inc. was filled as liquid crystal and then annealed in the conditions of at 80° C. for 1 hour.

COMPARATIVE EXAMPLE 2

Spacers for a liquid crystal display and a liquid crystal display were obtained by the same procedure as in Example 3 except for subjecting the reactant to a replacement reaction by a solvent after the completion of the reaction using cyclohexane (SP value=8.2) in preparation of a spacer for a liquid crystal display.

TABLE 1

| | Difference between contact angles of water (°) | Evaluation of spraying property | Evaluation of light leakage | |
|---|---|---|---|---|
| | | | in cutting off light | in vibration test |
| Example 1 | 3.0 | good | little-found | little-found |
| Example 2 | 7.0 | good | little-found | little-found |
| Comparative Example 1 | 0.3 | good | much light leakage was found | much light leakage was found |

EXAMPLE 3

(1) Preparation of Base Particles

The base particles prepared in Example 1 were used.

(2) Preparation of a Spacer for a Liquid Crystal Display

Into a separable flask, 50 parts by weight of the obtained base particles, 150 parts by weight of dimethylformamide (DMF), 10 parts by weight of methyl methacrylate (MMA) containing an alkyl group having 1 carbon atom, 70 parts by weight of isobutyl methacrylate (IBM) containing an alkyl group having 4 carbon atoms and 20 parts by weight of lauryl methacrylate (LMA) containing an alkyl group having 12 carbon atoms were charged and adequately dispersed with a sonicater, and then the mixture was stirred uniformly. After a nitrogen gas was introduced into a reaction system to adjust a system temperature to 50° C., a solution formed by dissolving 2.15 g of cerium ammonium nitrate in 100 g of 1N aqueous solution of nitric acid was added to this mixture and a reaction was continued for 4 hours.

After the completion of the reaction, the reactant was washed and further immersed in methanol (SP value=14.5)

EXAMPLE 4

(1) Preparation of Base Particle

The base particles prepared in Example 1 were used.

(2) Preparation of a Spacer for a Liquid Crystal Display

Into a separable flask, 50 parts by weight of the obtained base particles, 10 parts by weight of methyl methacrylate (MMA) containing an alkyl group having 1 carbon atom, 70 parts by weight of isobutyl methacrylate (IBM) containing an alkyl group having 4 carbon atoms and 20 parts by weight of lauryl acrylate (LA) containing an alkyl group having 12 carbon atoms were charged and adequately dispersed with a sonicater, and then the mixture was stirred uniformly. After a nitrogen gas was introduced into a reaction system to adjust a system temperature to 50° C., a solution obtainable by dissolving 2.15 g of cerium ammonium nitrate in 100 g of 1N aqueous solution of nitric acid was added to this mixture and a reaction was continued for 4 hours.

After the completion of the reaction, the reactant was washed and further immersed in methanol (SP value=14.5) and subjected to a replacement reaction by a solvent by being stirred for 12 hours in this state, and then dried to obtain a spacer for a liquid crystal display. And, a glass transition temperature of a coated polymer was 41° C. as a result of calculating according to the above equation (5).

(3) Fabrication of a Liquid Crystal Display

A liquid crystal display of a VA mode was fabricated using the obtained spacer for a liquid crystal display. As an alignment layer, there was used a solution obtainable by adding 1% of octadecyltrimethylammonium chloride to 3% aqueous solution of polyvinyl alcohol, and the direction a transmission axis of polarization of a polarizer was set at an angle of 45 degrees relative to the direction of rubbing and crossed Nicols was selected as the polarizer.

Spraying of the spacers for a liquid crystal display was conducted by means of a dry spray method using a spacer sprayer "DISPA-μA" manufactured by Nisshin Engineering Inc., and "MLC-6610" produced by Merck & Co., Inc. was filled as liquid crystal and then annealed in the conditions of at 80° C. for 1 hour.

ING SYSTEM G2 (manufactured by KRUSS GmbH). Incidentally, measurement of the contact angle was performed at room temperature of 25° C.

(B) with respect to the not-yet-treated spacers for a liquid crystal display and (A1) with respect to the annealed spacers for a liquid crystal display, which had been annealed at 80° C. for 1 hour and then cooled to 25° C., were respectively measured, and a difference between the contact angles before and after annealing (A1−B) was determined.

(Evaluation of a Spraying Property of Spacers for a Liquid Crystal Display)

Status in spraying the spacers in fabrication of a liquid crystal display was visually observed.

(Evaluation of Light Leakage of a Liquid Crystal Display)

The extent of light leakage of the liquid crystal display in cutting off light was visually observed. And in a vibration test, the extent of light leakage in striking the liquid crystal display for 1 minute with a hammer was visually observed.

TABLE 2

| | Contact angle of water (°) | | | | Evaluation of light leakage | |
|---|---|---|---|---|---|---|
| | contact angle A1 | contact angle B | difference between contact angles | Evaluation of spraying property | in cutting off light | in vibration test |
| Example 3 | 155.4 | 145.7 | 9.7 | good | little-found | little-found |
| Example 4 | 155.8 | 145.9 | 9.9 | good | little-found | little-found |
| Comparative Example 2 | 147.5 | 147.0 | 0.5 | cohesion of particles was found | much light leakage was found | much light leakage was found |
| Comparative Example 3 | 148.9 | 148.3 | 0.6 | cohesion of particles was found | much light leakage was found | much light leakage was found |

COMPARATIVE EXAMPLE 3

Spacers for a liquid crystal display and a liquid crystal display were obtained by the same procedure as in Example 4 except for subjecting the reactant to a replacement reaction by a solvent after the completion of the reaction using cyclohexane (SP value=8.2) in preparation of a spacer for a liquid crystal display.

(Evaluations)

Evaluations were performed by the following methods on the spacers for a liquid crystal display and the liquid crystal displays obtained in Examples 3, 4 and Comparative Examples 2, 3. The results of evaluations are shown in Table 2.

(Measurement of Contact Angles of Water on the Spacers for a Liquid Crystal Display Before and After Annealing)

A groove of 200 μm in depth was formed on the smoothed surface of glass by etching and after filling the spacers for a liquid crystal display in this groove, a pseudo plane, in which the spacers for a liquid crystal display were arrayed, was produced by pressing the spacers with a slide glass and sliding the slide glass while pressing the spacers. As a result of observing the surface of the pseudo plane with a microscope, it could be found that the spacers for a liquid crystal display formed a plurality of layers and the spacers for a liquid crystal display of the outermost layer aligned in close contact with one another.

A water droplet was formed on this pseudo plane in such a way that its diameter is about 1.5 mm and a contact angle of the water droplet was measured while recognizing the water droplet with a monitor using CONTACT ANGLE MEASUR-

INDUSTRIAL APPLICABILITY

In accordance with the present invention, it is possible to provide a spacer for a liquid crystal display and a method of producing a spacer for a liquid crystal display, which improve light leakage around a spacer for a liquid crystal display in cutting off light of a liquid crystal display and in vibrating a liquid crystal display and in addition have a good dry spraying property.

The invention claimed is:

1. A spacer for a liquid crystal display,
   which comprises a base particle and a polymer coating the surface of said base particle,
   a contact angle A1 of water on the spacer, measured at 25° C. when said spacer is annealed at a temperature of an annealing temperature T1 or higher in fabricating a liquid crystal display for 1 hour or more and then cooled, and a contact angle B of water on the spacer, measured at 25° C. without annealing the spacer, satisfying the relationship of the following equation (1):

$$A1-B \geq 1° \qquad (1).$$

2. The spacer for a liquid crystal display according to claim 1,
   wherein a contact angle A1 of water on the spacer, measured at 25° C. when said spacer is annealed at a temperature of an annealing temperature T1 or higher in fabricating a liquid crystal display for 1 hour or more and then cooled, and a contact angle B of water on the spacer, measured at room temperature without annealing the spacer, satisfy the relationship of the following equation (2):

$$A1-B \geqq 8°  \quad (2).$$

3. A spacer for a liquid crystal display,
which comprises a base particle and a polymer which coats the surface of said base particle,
a contact angle A2 of water on the spacer, measured at 25° C. when said spacer is annealed at a temperature of a glass transition temperature T2 or higher of said polymer and then cooled, and a contact angle B of water on the spacer, measured at 25° C. without annealing the spacer, satisfying the relationship of the following equation (3):

$$A2-B \geqq 1° \quad (3).$$

4. The spacer for a liquid crystal display according to claim 3,
wherein a contact angle A2 of water on the spacer, measured at 25° C. when the spacer is annealed at a temperature of a glass transition temperature T2 or higher of the polymer and then cooled, and a contact angle B of water on the spacer, measured at 25° C. without annealing the spacer, satisfy the relationship of the following equation (4):

$$A2-B \geqq 8° \quad (4).$$

5. The spacer for a liquid crystal display according to claim 1,
wherein the polymer contains a component containing an alkyl group having 10 or more carbon atoms in an amount 10% by weight or more and a component containing an alkyl group having 4 or less carbon atoms in an amount 50% by weight or more.

6. A method of producing a spacer for a liquid crystal display according to claim 1,
which comprises the steps of coating the surface of a base particle with a polymer, and immersing said base particle coated the surface with said polymer in a liquid medium having a SP value of 10 or higher and then drying the base particle.

7. The method of producing a spacer for a liquid crystal display according to claim 6,
wherein the liquid medium having a SP value of 10 or higher has a SP value of 12 to 15.

8. The method of producing a spacer for a liquid crystal display according to claim 6,
wherein the liquid medium having a SP value of 10 or higher contains methanol in an amount 50% by weight or more.

9. The spacer for a liquid crystal display according to claim 2,
wherein the polymer contains a component containing an alkyl group having 10 or more carbon atoms in an amount 10% by weight or more and a component containing an alkyl group having 4 or less carbon atoms in an amount 50% by weight or more.

10. The spacer for a liquid crystal display according to claim 3,
wherein the polymer contains a component containing an alkyl group having 10 or more carbon atoms in an amount 10% by weight or more and a component containing an alkyl group having 4 or less carbon atoms in an amount 50% by weight or more.

11. The spacer for a liquid crystal display according to claim 4,
wherein the polymer contains a component containing an alkyl group having 10 or more carbon atoms in an amount 10% by weight or more and a component containing an alkyl group having 4 or less carbon atoms in an amount 50% by weight or more.

12. A method of producing a spacer for a liquid crystal display according to claim 2,
which comprises the steps of coating the surface of a base particle with a polymer, and immersing said base particle coated the surface with said polymer in a liquid medium having a SP value of 10 or higher and then drying the base particle.

13. A method of producing a spacer for a liquid crystal display according to claim 3,
which comprises the steps of coating the surface of a base particle with a polymer, and immersing said base particle coated the surface with said polymer in a liquid medium having a SP value of 10 or higher and then drying the base particle.

14. A method of producing a spacer for a liquid crystal display according to claim 4,
which comprises the steps of coating the surface of a base particle with a polymer, and immersing said base particle coated the surface with said polymer in a liquid medium having a SP value of 10 or higher and then drying the base particle.

15. A method of producing a spacer for a liquid crystal display according to claim 5,
which comprises the steps of coating the surface of a base particle with a polymer, and immersing said base particle coated the surface with said polymer in a liquid medium having a SP value of 10 or higher and then drying the base particle.

16. The method of producing a spacer for a liquid crystal display according to claim 7,
wherein the liquid medium having a SP value of 10 or higher contains methanol in an amount 50% by weight or more.

17. A liquid crystal display comprising;
the spacer according to claim 1.
18. A liquid crystal display comprising;
the spacer according to claim 2.
19. A liquid crystal display comprising;
the spacer according to claim 3.

* * * * *